United States Patent [19]

Butler

[11] 4,452,990

[45] Jun. 5, 1984

[54] 1-AROYL-5-OXO-2-PYRROLIDINE-PROPANOIC ACIDS AND RELATED ESTERS

[75] Inventor: Donald E. Butler, Ann Arbor, Mich.

[73] Assignee: Warner-Lambert Company, Morris Plains, N.J.

[21] Appl. No.: 441,335

[22] Filed: Nov. 15, 1982

[51] Int. Cl.$^3$ .................. C07D 207/273; A61R 31/40
[52] U.S. Cl. ..................................... 548/543; 548/551
[58] Field of Search ............................... 548/551, 543

[56] References Cited

FOREIGN PATENT DOCUMENTS 53-5158  1/1978  Japan .................................... 548/551

Primary Examiner—Paul M. Coughlan, Jr.
Assistant Examiner—D. B. Springer
Attorney, Agent, or Firm—Jerry F. Janssen

[57] ABSTRACT

1-Aroyl-5-oxo-2-pyrrolidinepropanoic acids, salts, and esters which are useful as pharmacological agents, especially as agents for the reversal of amnesia, enhancing performance in poorly motivated subjects and treatment of senility and methods for their preparations are disclosed. Pharmaceutical compositions containing said compounds, salts, and esters and methods for using said compositions in treating senility, improving motivation and reversal of amnesia are also taught.

20 Claims, No Drawings

1-AROYL-5-OXO-2-PYRROLIDINEPROPANOIC ACIDS AND RELATED ESTERS

SUMMARY AND DETAILED DESCRIPTION

The present invention relates to 1-aroyl-5-oxo-2-pyrrolidinepropanoic acids, pharmaceutically acceptable salts, and esters thereof; methods for the production of the foregoing compounds; pharmaceutical compositions containing said compounds and others and methods for using the compounds in the treatment of senility, improving motivation in poorly performing subjects and reversing amnesia.

More specifically, the invention relates to compounds of the formula

Formula I wherein R is a pharmaceutically acceptable metal or amine cation, hydrogen, alkyl or where Z is hydrogen, alkyl fluoro, chloro, bromo or trifluoromethyl.

X and Y are hydrogen, chloro, fluoro, hydroxy, amino, alkylamino, dialkylamino, $(CH_2)_n N-$ where n is an integer from 3 to 7, alkoxy having from one to six carbon atoms or benzyloxy; X and Y may be the same or different and when X and Y are on adjacent carbon atoms, taken together may also include the group $-O-(CH_2)_2-O-$ or $-O-CH_2-O-$ pharmaceutically acceptable acid addition salts thereof with the proviso that when R is hydrogen, or a pharmaceutically acceptable metal or amine cation, X is a substituent other than hydrogen.

The term "alkyl" is intended to encompass a hydrocarbon group of from one to six carbon atoms, such as methyl, 2-propyl, cyclohexyl.

More preferred compounds are those wherein R is hydrogen, methyl, ethyl, benzyl, 2-chlorobenzyl, 3-chlorobenzyl, 4-chlorobenzyl, 4-trifluoromethylbenzyl, 4-methylbenzyl, sodium, potassium, calcium, ammonium, trimethylammonium or triethylammonium; X is 2-chloro, 4-chloro, 2-fluoro, 4-fluoro, 3-methyl, 2-methoxy, 3-methoxy or 4-methoxy and Y is hydrogen; X is 3-methyl, 3-benzyloxy or 3-hydroxy and Y is 4-methoxy and X and Y taken together is 3,4-methylenedioxy.

The most preferred compounds are those wherein R is hydrogen, sodium, potassium, calcium, magnesium or ammonium; X is 4-methoxy, 4-fluoro or 4-chloro and Y is hydrogen.

In addition, the invention is directed to methods for preparing the compounds of the invention.

The invention is also directed to pharmaceutical compositions containing a compound of the formula Formula II wherein $R^1$ is a pharmaceutically acceptable metal or amine cation, hydrogen, alkyl or where Z is hydrogen, alkyl fluoro, chloro, bromo or trifluoromethyl.

X and Y are hydrogen, chloro, fluoro, hydroxy, amino, alkylamino, dialkylamino, $(CH_2)_n N-$ where n is an integer from 3 to 7, alkoxy having from one to six carbon atoms or benzyloxy; X and Y may be the same or different and when X and Y are on adjacent carbon atoms, taken together may also include the group $-O-(CH_2)_2-O-$ and pharmaceutically acceptable acid addition salts thereof and a pharmaceutical carrier.

Lastly, the invention is directed to methods of treating senility, reversing amnesia and improving the performance of non-motivated subjects using the above described pharmaceutical compositions.

When basic groups, namely amino, alkylamino, dialkylamino or $(CH_2)_n N-,$ are present, the invention is intended to also encompass the pharmaceutically acceptable acid addition salts thereof, such as the hydrochloride, sulfate, phosphate, acetate, benzoate, etc.

1-Aroyl-5-oxo-2-pyrrolidinepropanoic acids and pharmaceutically acceptable salts and esters may exist in anhydrous forms as well as in solvated, including hydrated, forms. In general, the hydrated forms and the solvated forms are equivalent to the anhydrous or unsolvated forms for the purposes of the invention.

The compounds exist as d,l-isomers and the cognition activating activity may reside in one or the other of the pure isomers.

1-benzoyl-5-oxo-2-pyrrolidinepropanoic acid is a known compound reportedly prepared as a derivative of 5-oxo-2-pyrrolidinepropanoic acid by T. Lesiak and A. PrewyszKwinto, Roczniki Chemii (Poland), 45 (7/8), 1341-3 (1971).

Compounds of the invention of Formula I may be prepared as outlined in the following Synthetic Scheme:

In accordance with the invention, the foregoing compounds of Formula I except where X and Y are amino, alkylamino can be prepared by reacting the compound of Formula III

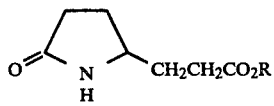

Formula III with an activated aroylating agent of the formula

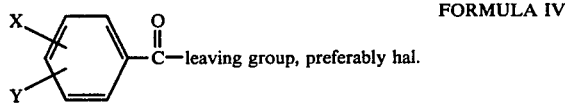

FORMULA IV where hal is F, Cl, or Br in the presence of an acid accepting base such as pyridine or a trialkyl amine. The reactants may be present in equimolar amounts although a slight excess of the aroyl halide and acid acceptor is preferred. The reaction is generally carried out in an inert solvent, such as diethylether, tetrahydrofuran, etc. at temperatures of from about 25° C. to 150° C., preferably at the boiling point of the inert solvent for from one to 96 hours.

The product may be isolated by crystallization, chromatography, or as a base addition salt by suitable adjustment of pH in the case of the free acid.

The pharmaceutically acceptable salts of the acid are prepared by adjusting the pH with the pharmaceutically acceptable base or by reacting the esters with the pharmaceutically acceptable base in a solvent and removing the solvent under reduced pressure.

In addition, compounds of Formula I wherein R is hydrogen may be prepared by catalytically reducing a compound of formula

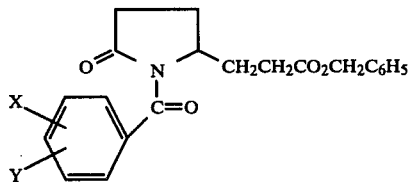

FORMULA V

This reaction is conducted in an inert solvent, such as tetrahydrofuran, in the presence of hydrogen and a noble metal, preferably palladium at temperatures of from about 0° C. to about 100° C., preferably at room temperature until the theoretical quantity of hydrogen is taken up by the reaction. The reaction is generally carried out at from atmospheric pressure to about 50 lbs per sq. in. of hydrogen.

The compounds of Formula I wherein X and Y are selected from the group consisting of amino, alkylamino, dialkylamino or

and pharmaceutically acceptable acid addition salts thereof are prepared from the corresponding nitro compound, namely where X and/or Y is nitro. This is achieved by the following procedures.

The nitro compounds (VI) are prepared by the above described general procedure for preparing compounds of the invention. Namely, a compound of Formula III is reacted with a compound of Formula IV wherein X and/or Y are nitro.

The nitro group is reduced to an amino group by a catalytic hydrogenation procedure using a noble metal, preferably palladium or nickel and a positive hydrogen pressure. The reaction is conducted in an inert solvent, such as tetrahydrofuran, ethanol, etc. at or about room temperature until the theoretical quantity of hydrogen is absorbed for the reaction to be complete.

The amino compounds of the invention (VII) may be converted to the corresponding pharmaceutically acceptable acid addition salts by treatment with a pharmaceutically acceptable acid, such as hydrochloric acid, sulfuric acid, phosphoric acid, acetic acid, benzoic acid, etc. This process can take place during the reduction by carrying out the reaction in an acidic medium.

The compounds of the Formula VII where X and Y are amino are converted to the corresponding alkylamino compounds of the invention (VIII) by (a) direct alkylation using an alkylating reagent, such as an alkyl bromide, iodide, sulfate, etc. (b) forming an imine by reaction with an aldehyde and reducing the imine to the desired alkyl amino compound or (c) formation on an imine using benzaldehyde and quaternizing this compound with an alkylating reagent, such as an alkylbromide, iodide, sulfate, etc. and hydrolytically removing the benzylidene group.

The compounds of the invention where X and/or Y are dialkylamino are prepared by direct alkylation of compounds of the formula VII or VIII using an alkylating reagent, such as an alkylbromide, iodide, sulfate, etc.

The compounds of the invention where X and/or Y are

are prepared by direct alkylation using a compound of the formula L.G.—(CH$_2$)$_n$—L.G. where L.G. is bromo, iodo, sulfonate, etc.

The above described alkylamino, dialkylamino and

substituted compounds may be converted to the corresponding pharmaceutically acceptable acid addition salt by treatment with pharmaceutically acceptable acids, such as hydrochloric acid, sulfuric acid, phosphoric acid, acetic acid, benzoic acid, etc.

The above described reactions for preparing alkylamino, dialkylamino and

containing compounds are carried out in inert solvents at temperatures of from 0° C. to about 120° C., preferably 20° C. to 80° C. The reactions may take from a few minutes to a number of days depending upon temperature and substituents. The most critical factor appears to be ratio of reactants which must be adjusted especially when directly alkylating so as to avoid the introduction of more alkyl groups than desired. This is achieved by using an excess of the amino compound to be alkylated.

The necessary starting material III where R is $CH_3$ or $C_2H_5$ are known compounds synthesized as intermediates in the following publications which are incorporated by reference.

R. Lukes and F. Sorm; Coll. Czechoslov. Chem. Commun., 12, 278–291 (1947).

N. J. Leonard, L. R. Hruda, and F. W. Long; J. Amer. Chem. Soc., 69, 690–692 (1947).

Additional necessary starting materials of type III are synthesized by reaction of a compound of the Formula IX

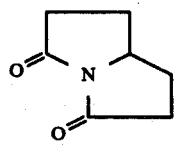

Formula IX with an excess of the requisite benzylalcohol of the Formula X

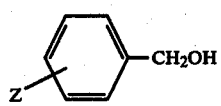

Formula X in the presence of a catalytic amount of an acid catalyst, such as a trace of hydrogen chloride, hydrogen bromide, or other strong acid.

Compound IX is synthesized as in the above-described Leonard, et al. and Lukes and Sorm references.

Also in accordance with the invention, pharmaceutical compositions may be produced by formulation 1-aroyl-5-oxo-2-pyrrolidinepropanoic acids, pharmaceutically acceptable salts or esters in unit dosage form with a pharmaceutical carrier. Some examples of unit dosage forms are tablets, capsules, lozenges, and pills; as well as powders and aqueous and nonaqueous solutions and suspensions packaged in containers containing either one or some larger number of dosage units and capable of being sub-divided into individual doses by such means as measurements into teaspoon or other standard container. Some examples of suitable pharmaceutical carriers, including pharmaceutical diluents, are sugars such as lactose and sucrose; starches such as corn starch and potato starch; cellulose derivatives such as sodium carboxymethyl cellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma; propylene glycol; glycerine; sorbitol; polyethylene glycol; water; agar; alginic acid; as well as other compatible substances normally used in pharmaceutical formulations. The compositions of the invention can also contain other components such as coloring agents, flavoring agents, and/or preservatives. These materials, if present, are usually used in relatively small amounts. The compositions can, if desired, also contain other therapeutic agents.

The percentage of the active ingredient in the foregoing compositions can be varied within wide limits but for practical purposes it is preferably present in a concentration of at least 10% in a solid composition and at least 2% in a primarily liquid composition. The most satisfactory compositions are those in which a much higher proportion of the active ingredient is present. The compositions of the invention preferably contain from 1 to 500 mg, preferably 5 to 100 mg of the active ingredient per dosage unit so that the entire amount to be administered during a day can be made up from a reasonable number of dosage units.

1-Aroyl-5-oxo-2-pyrrolidinepropanoic acids, pharmaceutically acceptable salts and esters may be incorporated into formulations intended for parenteral administration. Such compositions may be in a powdered form intended to be combined with an isotonic solution containing other ingredients such as preservatives, etc.

1-Aroyl-5-oxo-2-pyrrolidinepropanoic acids, pharmaceutically acceptable salts and esters may be incorporated into suppository formulations intended for rectal administration. Generally the carrier is cocoa butter or glycerine.

The mammalian dosage range for a 70 kg subject is from 0.1 to 100 mg/kg of body weight per day or preferably 1 to 50 mg/kg of body weight per day optionally in divided portions. Thus a daily dose for an average 70 kg subject would be 7 to 700 mg, preferably 70 mg to 350 mg.

The effectiveness of the aforementioned compound is determined by a test designed to show a compound's ability to reverse amnesia produced by electroconvulsive shock. The test is fully described in U.S. Pat. No. 4,145,347, issued Mar. 20, 1979, and is herein incorporated by reference. The only difference being that the test compounds in the present instance are administered orally and the length of electroconvulsive shock is 1.0 seconds.

The following criteria are used in interpreting the percent of amnesia reversal scores: 40 percent or more (active=A); 25 to 39 percent (borderline=C) and 0 to 24 percent (inactive=N).

Table 1 below reports the percent of amnesia reversal of orally administered 1-Aroyl-5-oxo-2-pyrrolidine-propanoic acids.

TABLE 1

| Aroyl Substituent | Dose mg/kg = | 100 | 32 | 10 | 3.2 | 1.00 | 0.32 |
|---|---|---|---|---|---|---|---|
| 4-$CH_3O$— | % Amnesia | 70 (A) | 77 (A) | 92 (A) | 31 (A) | 31 (C) | 15 (N) |
| 3-HO, 4-$CH_3O$ | Reversal (Rating) | 21 (N) | | 31 (C) | | 2 (N) | |
| 4-H* | | 60 (A) | | 54 (A) | | 45 (A) | |
| Replication | | 45 (A) | | 25 (C) | | 27 (C) | |

*The 1-benzoyl compound is apparently not as active as the 4-$CH_3O$— since on replication the results were not as positive. In addition, a third test was completely inactive. This was probably a faulty test.

TABLE 2

| 1-Aroyl-5-oxo-2-pyrrolidinepropanoic Acid Esters | | | | | |
|---|---|---|---|---|---|
| Aroyl Substituent | Ester | Dose mg/kg = | 100 | 10 | 1 |
| 4-$CH_3O$— | $CH_2C_6H_5$ | % Amnesia | 0 (N) | 73 (A) | 67 (A) |
| 3-$C_6H_5CH_2O$—, 4-$CH_3O$ | $CH_2C_6H_5$ | Reversal | 0 (N) | 0 (N) | 40 (A) |
| 4-H | $CH_2C_6H_5$ | (Rating) | 78 | 100 | 96 |

TABLE 2-continued

1-Aroyl-5-oxo-2-pyrrolidinepropanoic Acid Esters

| Aroyl Substituent | Ester | Dose mg/kg = | 100 | 10 | 1 |
|---|---|---|---|---|---|
| | | | (A) | (A) | (A) |

Preparation of 1-Benzoyl-5-oxo-2-pyrrolidinepropanoic acid and benzyl ester

A solution of 24.7 g of 5-oxo-2-pyrrolidinepropanoic acid benzyl ester in 800 ml of tetrahydrofuran is treated with 14.1 g of benzoyl chloride. The mixture is heated to 55° C. and a solution of 20 g of triethylamine in 400 ml of tetrahydrofuran is added dropwise over a two hour period. The mixture is stirred and heated at 55° C. for 16 hours. The warm mixture is filtered through filter aid to remove triethylamine hydrochloride and concentrated at reduced pressure.

The mixture of 1-benzoyl-5-oxo-2-pyrrolidinepropanoic acid benzyl ester and 5-benzoyloxy-4,5-dehydro-2-pyrrolidinepropanoic acid benzyl ester is separated by chromatography over silica gel using methylene chloride:diethylether (25:1) on a Waters Prep 500A HPLC instrument. The desired fractions are concentrated at reduced pressure finally at 100° C. and 0.1 mm pressure to yield 1-benzoyl-5-oxo-2-pyrrolidinepropanoic acid benzyl ester as an analytically pure oil with the following characteristic proton NMR spectrum: $^1$HNMR (CDCl$_3$) δ 1.7–2.8 (m,8H), 4.5 (m,1H), 5.1 (s,2H), 7.3–7.7 (m, 10H).

A solution of 8.6 g of 1-benzoyl-5-oxo-2-pyrrolidinepropanoic acid benzyl ester in 200 ml of tetrahydrofuran is treated with 2 g of 20% Pd/C catalyst and hydrogen gas. After theoretical hydrogen uptake, the mixture is filtered through filter aid. The solution is concentrated at reduced pressure and the oily product is triturated with anhydrous diethyl ether to yield after drying in vacuo 1-benzoyl-5-oxo-2-pyrrolidinepropanoic acid, mp 117°–119° C.

Preparation of 1-(4-methoxybenzoyl)-5-oxo-2-pyrrolidinepropanoic acid and benzyl ester A solution of 50 g of 5-oxo-2-pyrrolidinepropanoic acid benzyl ester in 800 ml of tetrahydrofuran is treated with 28.3 g of 4-methoxybenzoyl chloride. The mixture is heated to 55° C. and a solution of 20 g of triethylamine in 400 ml of tetrahydrofuran is added dropwise over a two hour period. The mixture is stirred and heated at 55° C. for 16 hours. The warm mixture is filtered through filter aid to remove triethylamine hydrochloride and concentrated at reduced pressure. Chromatography over silica using a Waters Prep 500 HPLC apparatus yielded 1-(4-Methoxybenzoyl)-5-oxo-2-pyrrolidinepropanoic acid benzyl ester mp 80°–83° C. After concentration and crystallization.

A solution of 19 g of 1-(4-methoxybenzoyl)-5-oxo-2-pyrrolidinepropanoic acid benzyl ester in 200 ml of tetrahydrofuran is treated with 2 g of 20% Pd/C catalyst and hydrogen gas. After theoretical hydrogen uptake, the mixture is filtered through filter aid. The solution is concentrated at reduced pressure and the oily product is triturated with anhydrous diethyl ether to yield after drying in vacuo 1-(4-methoxybenzoyl)-5-oxo-2-pyrrolidinepropanoic acid, mp 130°–133° C.

Preparation of 1-(4-chlorobenzoyl)-5-oxo-2-pyrrolidinepropanoic acid and benzyl ester A solution of 24.7 g of 5-oxo-2-pyrrolidinepropanoic acid benzyl ester in 800 ml of tetrahydrofuran is treated with 19.3 g of 4-chlorobenzoyl chloride. The mixture is heated to 55° C. and a solution of 10.1 g of triethylamine in 400 ml of tetrahydrofuran is added dropwise over a two hour period. The mixture is stirred and heated at 55° C. for 16 hours. The warm mixture is filtered through filter aid to remove triethylamine hydrochloride and concentrated at reduced pressure.

The mixture of 1-(4-chlorobenzoyl)-5-oxo-2-pyrrolidinepropanoic acid benzyl ester and 5-[(4-chlorobenzoyloxy)-4,5-dehydro-2-pyrrolidinepropanoic acid benzyl ester is separated by chromatography over silica gel using methylene chloride:diethyl ester (25:1) on a Waters Prep 500A HPLC instrument. The desired fractions are concentrated at reduced pressure to yield 1-(4-chlorobenzoyl)-5-oxo-2-pyrrolidinepropanoic acid benzyl ester as an analytically pure oil with the following chracteristic proton NMR spectrum: $^1$HNMR (CDCl$_3$) δ 1.7–2.8 (m, 8H), 4.5 (n, 1H), 5.1 (s, 2H), 7.2–7.6 (m, 9H).

A solution of 7.6 g of 1-(4-chlorobenzoyl)-5-oxo-2-pyrrolidinepropanoic acid benzyl ester in 200 ml of tetrahydrofuran is treated with 2 g of 20% Pd/C catalyst and hydrogen gas. After theoretical hydrogen uptake, the mixture is filtered through filter aid. The solution is concentrated at reduced pressure and the oily product is triturated with anhydrous diethyl ether to yield after drying in vacuo 1-(4-chlorobenzoyl)-5-oxo-2-pyrrolidinepropanoic acid, mp 141°–143° C.

Preparation of 1-(2-methoxybenzoyl)-5-oxo-2-pyrrolidinepropanoic acid and benzyl ester A solution of 24.7 g of 5-oxo-2-pyrrolidinepropanoic acid benzyl ester in 800 ml of tetrahydrofuran is treated with 18.8 g of 2-methoxybenzoyl chloride. The mixture is heated to 55° C. and a solution of 20 g of triethylamine in 400 ml of tetrahydrofuran is added dropwise over a two hour period. The mixture is stirred and heated at 55° C. for 16 hours. The warm mixture is filtered through filter aid to remove triethylamine hydrochloride and concentrated at reduced pressure.

The mixture of 1-(2-methoxybenzoyl)-5-oxo-2-pyrrolidinepropanoic acid benzyl ester and 5-(2-methoxybenzoyloxy)-4,5-dehydro-2-pyrrolidinepropanoic acid benzyl ester is separated by chromatography over silic gel using methylene chloride:diethyl ether (25:1) on a Waters Prep 500A HPLC instrument. The desired fractions are concentrated at reduced pressure finally at 100° C. and 0.1 mm pressure to yield 1-(2-methoxybenzoyl)-5-oxo-2-pyrrolidinepropanoic acid benzyl ester as an analytically pure oil with the following characteristic proton NMR spectrum: $^1$HNMR (CDCl$_3$) δ 1.7–2.8 (m, 8H), 3.7 (s, 3H), 4.5 (m, 1H), 5.1 (s, 2H), 7.0–7.6 (m, 9H).

A solution of 5.4 g of 1-(2-methoxybenzoyl)-5-oxo-2-pyrrolidinepropanoic acid benzyl ester in 200 ml of tetrahydrofuran is treated with 2 g of 20% Pd/C catalyst and hydrogen gas. After theoretical hydrogen uptake, the mixture is filtered through filter aid. The solution is concentrated at reduced pressure and the oily product is triturated with anhydrous diethyl ether to yield after drying in vacuo 1-(2-methoxybenzoyl)-5- oxo-2-pyrrolidinepropanoic acid, as an oil with the following characteristic proton NMR spectrum $^1$HNMR (CDCl$_3$) δ 1.5–2.78 (M,8H), 3.78 (s,3H), 4.58 (m,1H), 6.7–7.3 (m,4H).

Preparation of 1-(4-fluorobenzoyl)-5-oxo-2-pyrrolidinepropanoic acid and benzyl ester A solution of 24.7 g of 5-oxo-2-pyrrolidinepropanoic acid benzyl ester in 800 ml of tetrahydrofuran is treated with 17.4 g of 4-fluorobenzoyl chloride. The mixture is heated to 55° C. and a solution of 10.1 g of triethylamine in 400 ml of tetrahydrofuran is added dropwise over a two hour period. The mixture is stirred and heated at 55° C. for 16 hours. The warm mixture is filtered through filter aid to remove triethylamine hydrochloride and concentrated at reduced pressure.

The mixture of 1-(4-fluorobenzoyl)-5-oxo-2-pyrrolidinepropanoic acid benzyl ester and 5-(4-fluorobenzoyloxy)-4,5-dehydro-2-pyrrolidinepropanoic acid benzyl ester is separated by chromatography over silica gel using methylene chloride:diethyl ether (25:1) on a Waters Prep 500A HPLC instrument. The desired fractions are concentrated at reduced pressure finally at 100° C. and 0.1 mm pressure to yield 1-benzoyl-5-oxo-2-pyrrolidinepropanoic acid benzyl ester as an analytically pure oil with following characteristic proton NMR spectrum: $^1$HNMR (CDCl$_3$) δ 1.7–2.8 (m, 8H), 4.5 (m, 1H), 5.1 (s, 2H), 7.0–7.7 (m, 9H).

A solution of 19 g of 1-(4-fluorobenzoyl)-5-oxo-2-pyrrolidinepropanoic acid benzyl ester in 200 ml of tetrahydrofuran is treated with 2 g of 20% Pd/C catalyst and hydrogen gas. After theoretical hydrogen uptake, the mixture is filtered through filter aid. The solution is concentrated at reduced pressure and the oily product is triturated with anhydrous diethyl ester to yield after drying in vacuo 1-(4-fluorobenzoyl)-5-oxo-2-pyrrolidinepropanoic acid, mp 133°–135° C.

Preparation of 1-(3-methoxybenzoyl)-5-oxo-2-pyrrolidine propanoic acid and benzyl ester A solution of 24.7 g of 5-oxo-2-pyrrolidinepropanoic acid benzyl ester in 800 ml of tetrahydrofuran is treated with 18.8 g of 3-methoxybenzoyl chloride. The mixture is heated to 55° C. and a solution of 10.1 g of triethylamine in 400 ml of tetrahydrofuran is added dropwise over a two hour period. The mixture is stirred and heated at 55° C. for 16 hours. The warm mixture is filtered through filter aid to remove triethylamine hydrochloride and concentrated at reduced pressure.

The mixture of 1-(3-methoxybenzoyl)-5-oxo-2-pyrrolidinepropanoic acid benzyl ester and 5-(3-methoxybenzoyloxy)-4,5-dehydro-2-pyrrolidinepropanoic acid benzyl ester is separated by chromatography over silica gel using methylene chloride:diethyl ether (25:1) on a Waters Prep 500A HPLC instrument. The desired fractions are concentrated at reduced pressure finally at 100° C. and 0.1 mm pressure to yield 1-(3-methoxybenzoyl)-5-oxo 2-pyrrolidinepropanoic acid benzyl ester as an analytically pure oil with the following characteristic proton NMR spectrum: $^1$HNMR (CDCl$_3$) δ1.7–2.8 (m, 8H), 3.7 (s, 3H), 4.5 (m, 1H) 5.1 (s, 2H), and 7.3–7.7 (m, 10H).

A solution of 19 g of 1-(3-methoxybenzoyl)-5-oxo-2-pyrrolidinepropanoic acid benzyl ester in 200 ml of tetrahydrofuran is treated with 2 g of 20% Pd/C catalyst and hydrogen gas. After theoretical hydrogen uptake, the mixture is filtered through filter aid. The solution is concentrated at reduced pressure and the oily product is triturated with anhydrous diethyl ether to yield after drying in vacuo 1-(3-methoxybenzoyl)-5-oxo-2-pyrrolidinepropanoic acid, mp 79°–81° C.

Preparation of 1-(3-hydroxy-4-methoxybenzoyl)-5-oxo-2-pyrrolidinepropanoic acid and 1-(3-benzyloxy-4-methoxybenzoyl)-5-oxo-2-pyrrolidinepropanoic acid benzyl ester A solution of 13 g of 5-oxo-2-pyrrolidinepropanoic acid benzyl ester in 250 ml of tetrahydrofuran is treated with 14.0 g of 3-benzyloxy-4-methoxybenzoyl chloride. The mixture is heated to 55° C. and a solution of 5.5 g of triethylamine in 400 ml of tetrahydrofuran is added dropwise over a two hour period. The mixture is stirred and heated at 55° C. for 16 hours. The warm mixture is filtered through filter aid to remove triethylamine hydrochloride and concentrated at reduced pressure. Chromatography over silica using a Waters Prep 500 HPLC apparatus yields 1-(3-benzyloxy-4-methoxybenzoyl)-5-oxo-2-pyrrolidinepropanoic acid benzyl ester with mp 92°–95° C. after concentration and crystallization.

A solution of 7.4 g of 1-(3-benzyloxy-4-methoxybenzoyl)-5-oxo-2-pyrrolidinepropanoic acid benzyl ester in 100 ml of tetrahydrofuran is treated with 2 g of 20% Pd/C catalyst and hydrogen gas. After theoretical hydrogen uptake, the mixture is filtered through filter aid. The solution is concentrated at reduced pressure and the oily product is triturated with anhydrous diethyl ether to yield after drying in vacuo 1-(3-hydroxy-4-methoxybenzoyl)-5-oxo-2-pyrrolidinepropanoic acid, mp 159°–162° C.

Preparation of 5-oxo-pyrrolidinepropanoic acid benzyl ester

Twenty-eight grams of dihydro 1H-pyrrolizine-3,5 (2H, 6H) dione is dissolved in 76 g of benzyl alcohol and 0.2 ml of concentrated hydrochloric acid is added. The solution is heated at 98° C. for 104 hours. The mixture is cooled and excess benzyl alcohol is distilled at 0.1 mm pressure to a maximum bath temperature of 100° C. The residual oil is dissolved in 1 l of anhydrous diethylether, 1 g of activated charcoal is added and the resulting suspension is filtered through filter aid. The filtrate is concentrated at reduced pressure and the resulting crystals are isolated by filtration. Recrystallization from cyclohexane containing 12% methylene chloride yields 5-oxo-2-pyrrolidinepropanoic acid benzyl ester with a melting point of 79°–80° C.

Preparation of 5-oxo-2-pyrrolidinepropanoic acid methyl ester

Twenty-eight grams of dihydro 1H-pyrrolizine-3,5 (2H, 6H) dione is dissolved in 100 g of methyl alcohol and 0.2 ml of concentrated hydrochloric acid is added. The solution is heated at reflux for 104 hours. The mixture is cooled and excess methyl alcohol is distilled at reduced pressure. The residual oil is dissolved in 1 l of anhydrous diethylether, 1 g of activated charcoal is added and the resulting suspension is filtered through filter aid. The filtrate is concentrated at reduced pressure and the resulting crystals are isolated by filtration. Recrystallization from methanol yields 5-oxo-2-pyrrolidinepropanoic acid methyl ester with a melting point of 52°–53° C.

Preparation of 5-oxo-2-pyrrolidinepropanoic acid ethyl ester

Twenty-eight grams of dihydro 1H-pyrrolizine-3,5 (2H, 6H) dione is dissolved in 100 g of ethyl alcohol and 0.2 ml of concentrated hydrochloric acid is added. The solution is heated at reflux for 104 hours. The mixture is cooled and excess ethyl alcohol is distilled at reduced pressure. The oil is dissolved in 1 l of anhydrous diethylether, 1 g of activated charcoal is added and the resulting suspension is filtered through filter aid. The filtrate is concentrated at reduced pressure and the resulting crystals are isolated by filtration. Recrystallization from carbon tetrachloridepetroleum ether yields 5-oxo-2-pyrrolidinepropanoic acid ethyl ester with a melting point of 60°–61° C.

Preparation of 5-oxo-2-pyrrolidinepropanoic acid o-chlorobenzyl ester

Five grams of dihydro 1H-pyrrolizine-3,5(2H, 6H) dione is dissolved in 31 g of o-chlorobenzyl alcohol and 0.2 ml of concentrated hydrochloric acid is added. The solution is heated at 100° C. for 71 hours. The mixture is cooled and dissolved in 150 ml of anhydrous diethylether. The solution is cooled to induce crystallization and the resulting crystals are isolated by filtration. Recrystallization from toluene-diethyl ether yields 5-oxo-2-pyrrolidinepropanoic acid o-chlorobenzyl ester with a melting point of 99°–100° C.

Preparation of 5-oxo-2-pyrrolidinepropanoic acid m-chlorobenzyl ester

Two hundred and eighty eight milligrams of dihydro 1H-pyrrolizine-3,5(2H, 6H) dione is dissolved in 600 mg of m-chlorobenzyl alcohol and 0.2 ml of concentrated hydrochloric acid is added. The solution is heated at 100° C. for 40 hours. The mixture is cooled and is dissolved in 50 ml of anhydrous diethylether. The filtrate is cooled to induce crystallization and the resulting crystals are isolated by filtration. Recrystallization from toluene-petroleum ether yields 5-oxo-2-pyrrolidinepropanoic acid m-chlorobenzyl ester with a melting point of 90°–91° C.

Preparation of 5-oxo-2-pyrrolidinepropanoic acid p-chlorobenzyl ester

Five grams of dihydro 1H-pyrrolizine-3,5(2H, 6H) dione is dissolved in 31 g of p-chlorobenzyl alcohol and 0.2 ml of concentrated hydrochloric acid is added. The solution is heated at 100° C. for 65 hours. The mixture is cooled and chromatographed over silica gel in dichloromethane. The starting p-chlorobenzyl alcohol is eluted with dichloromethane and the product is eluted with 2.5% methanol in dichloromethane. The eluate containing the product is concentrated at reduce pressure and the residual oil solidifies upon standing. The solid is recrystallized from toluene-diethyl ether to yield 5-oxo-2-pyrrolidinepropanoic acid p-chlorobenzyl ester with a melting point of 63°–64° C.

Preparation of 5-oxo-2-pyrrolidinepropanoic acid p-trifluoromethylbenzylester Five grams of dihydro 1H-pyrrolizine-3,5(2H, 6H) dione is dissolved in 29 g of benzyl alcohol and 0.2 ml of concentrated hydrochloric acid is added. The solution is heated at 100° C. for 72 hours. The mixture is cooled and chromatographed over silica gel in dichloromethane. The starting p-trifluoromethylbenzyl alcohol is eluted with dichloromethane and the product is eluted with 1.0% methanol in dichloromethane. The eluate containing the product is concentrated at reduced pressure and the residual oil solidifies upon standing. The solid is recrystallized from toluene-diethyl ether to yield 5-oxo-2-pyrrolidinepropanoic acid p-trifluoromethylbenzyl ester with a melting point of 81°–82° C.

Preparation of 5-oxo-2-pyrrolidinepropanoic acid p-methylbenzyl ester

Five grams of dihydro 1H-pyrrolizine-3,5(2H, 6H) dione is dissolved in 27 g of p-methylbenzyl alcohol and 0.2 ml of concentrated hydrochloric acid is added. The solution is heated at 100° C. for 48 hours. The mixture is cooled and chromatographed over silica gel in dichloromethane. The starting p-methylbenzyl alcohol is eluted with dichloromethane and the product is eluted with 1.0% methanol in dichloromethane. The eluate containing the product is concentrated at reduce pressure and the residual oil solidifies upon standing. The solid is recrystallized from toluene-diethyl ether to yield 5-oxo-2-pyrrolidinepropanoic acid p-methylbenzyl ester with a melting point of 71°–72° C.

The invention is further illustrated by the following Examples of tablets containing 1.0, 2.5, 25, 50 mg; capsules containing 1.0, 2.5, 25, 50 mg respectively of active ingredient, an example of a parenteral formulation, an example of a Rectal Suppository formulation, an example of a Suspension formulation and an example of a Syrup for Reconstitution.

EXAMPLE 1

| Ingredient | Quantity |
| --- | --- |
| 1-Benzoyl-5-oxo-2-pyrrolidinepropanoic acid | 150 g |
| Lactose | 1124 g |
| Corn Starch | 39 g |
| Hydroxypropyl cellulose | 30 g |
| Magnesium stearate | 7 g |
| Ethanol-water 50:50 | qs |

The 1-benzoyl-5-oxo-2-pyrrolidinepropanoic acid, lactose, and hydroxypropyl cellulose are blended and granulated with 50:50 ethanol-water. The wet granulation is screened, dried, and rescreened. The resulting dried granulation is blended with magnesium stearate and the corn starch and the mixture is compressed into 225 mg tablets using an 11/32 inch standard concave punch. Yield equals approximately 6000 tablets each containing 25.0 mg of 1-benzoyl-5-oxo-2-pyrrolidinepropanoic acid.

EXAMPLE 2

| Ingredient | Quantity |
| --- | --- |
| 1-Benzoyl-5-oxo-2-pyrrolidinepropanoic acid | 15 g |
| Lactose | 1249 g |
| Corn Starch | 39 g |
| Hydroxypropyl cellulose | 30 g |
| Magnesium stearate | 7 g |
| Ethanol-water 50:50 | qs |

The 1-benzoyl-5-oxo-2-pyrrolidinepropanoic acid, lactose, and hydroxypropyl cellulose are blended and granulated with 50:50 ethanol-water. The wet granulation is screened, dried, and rescreened. The resulting dried granulation is blended with magnesium stearate and the corn starch and the mixture is compressed into 225 mg tablets using an 11/32 inch standard concave punch. Yield equals approximately 6000 tablets each containing 2.5 mg of 1-benzoyl-5-oxo-2-pyrrolidine-propanoic acid.

EXAMPLE 3

| Ingredient | Quantity |
|---|---|
| 1-Benzoyl-5-oxo-2-pyrrolidine-propanoic acid | 6 g |
| Lactose | 1268 g |
| Corn Starch | 39 g |
| Hydroxypropyl cellulose | 30 g |
| Magnesium stearate | 7 g |
| Ethanol-water 50:50 | qs |

The 1-benzoyl-5-oxo-2-pyrrolidinepropanoic acid, lactose, and hydroxypropyl cellulose are blended and granulated with 50:50 ethanol-water. The wet granulation is screened, dried, and rescreened. The resulting dried granulation is blended with magnesium stearate and the corn starch and the mixture is compressed into 225 mg tablets using an 11/32 inch standard concave punch. Yield equals approximately 6000 tablets each containing 1.0 mg of 1-benzoyl-5-oxo-2-pyrrolidine-propanoic acid.

EXAMPLE 4

| Ingredient | Quantity |
|---|---|
| 1-Benzoyl-5-oxo-pyrrolidine-propanoic acid | 300 g |
| Lactose | 974 g |
| Corn Starch | 39 g |
| Hydroxypropyl cellulose | 30 g |
| Magnesium stearate | 7 g |
| Ethanol-water 50:50 | qs |

The 1-Benzoyl-5-oxo-2-pyrrolidinepropanoic acid, lactose, and hydroxypropyl cellulose are blended and granulated with 50:50 ethanol-water. The wet granulation is screened, dried, and rescreened. The resulting dried granulation is blended with magnesium stearate and the corn starch and the mixture is compressed into 225 mg tablets using an 11/32 inch standard concave punch. Yield equals approximately 6000 tablets each containing 50.0 mg of 1-benzoyl-5-oxo-2-pyrrolidine-propanoic acid.

EXAMPLE 5

| Ingredient | Quantity |
|---|---|
| 1-Benzoyl-5-oxo-2-pyrrolidine-propanoic acid | 250 g |
| Lactose | 1723 g |
| Magnesium stearate | 27 g |

The mixture is blended and filled into No. 4 hard gelatin capsules, filling each capsule with 200 mg of the powder mixture. Yield equals approximately 10,000 capsules each containing 25.0 mg of 1-benzoyl-5-oxo-2-pyrrolidinepropanoic acid.

EXAMPLE 6

| Ingredient | Quantity |
|---|---|
| 1-Benzoyl-5-oxo-2-pyrrolidine-propanoic acid | 25 g |
| Lactose | 1948 g |
| Magnesium stearate | 27 g |

The mixture is blended and filled into No. 4 hard gelatin capsules, filling each capsule with 200 mg of the powder mixture. Yield equals approximately 10,000 capsules each containing 2.5 mg of 1-benzoyl-5-oxo-2-pyrrolidinepropanoic acid.

EXAMPLE 7

| Ingredient | Quantity |
|---|---|
| 1-Benzoyl-5-oxo-2-pyrrolidine-propanoic acid | 10 g |
| Lactose | 1963 g |
| Magnesium stearate | 27 g |

The mixture is blended and filled into No. 4 hard gelatin capsules, filling each capsule with 200 mg of the powder mixture. Yield equals approximately 10,000 capsules each containing 1.0 mg of 1-benzoyl-5-oxo-2-pyrrolidinepropanoic acid.

EXAMPLE 8

| Ingredient | Quantity |
|---|---|
| 1-Benzoyl-5-oxo-2-pyrrolidine-propanoic acid | 500 g |
| Lactose | 1473 g |
| Magnesium stearate | 27 g |

The mixture is blended and filled into No. 4 hard gelatin capsules, filling each capsule with 200 mg of the powder mixture. Yield equals approximately 10,000 capsules each containing 50.0 mg of 1-benzoyl-5-oxo-2-pyrrolidinepropanoic acid.

EXAMPLE 9

| Ingredient | Quantity |
|---|---|
| 1-Benzoyl-5-oxo-2-pyrrolidine-propanoic acid | 30 mg |
| Witepsol H35 | 1.97 g |

The Witepsol H35 is melted by heating to 38° C., 1-benzoyl-5-oxo-2-pyrrolidinepropanoic acid is added and mixed until thoroughly dispersed and placed in a mold at 33°–34° C.

The suppository can contain a range of active ingredient from 30 mg to 500 mg.

EXAMPLE 10

| Ingredient | Quantity |
|---|---|
| 1-Benzoyl-5-oxo-2-pyrrolidine-propanoic acid | 10 g |
| Saccharin Sodium | 0.5 g |
| Thihydroxysterain | 0.75 g |
| Propylparaben | 0.1 g |
| Imitation Cherry Flavor | 2 ml |

| Ingredient | Quantity |
| --- | --- |
| Neobee M-5 q.s. ad | 100 ml |

Propylparaben is dissolved in a portion of the Neobee M-5, the trihydroxystearin is added and the mixture is homogenized for 30 minutes while maintaining the temperature between 50°–60° C. The mixture is cooled and the 1-Benzoyl-5-oxo-2-pyrrolidinepropanoic acid, saccharin sodium and imitation cherry flavor are added. The volume is made up with Neobee M-5.

The suspension can contain between 50 mg/5 ml and 500 mg/5 ml.

EXAMPLE 11

| Ingredient | Quantity |
| --- | --- |
| 1-Benzoyl-5-oxo-2-pyrrolidine-propanoic acid | 10 g |
| Sugar granulated, Bottlers grade | 60 g |
| Artificial Peppermint Flavor, Water soluble (American Flavor and Fragrance) | 0.4 g |
| Water q.s. ad | 100 ml |

The 1-benzoyl-5-oxo-2-pyrrolidinepropanoic acid, granulated sugar, and artificial peppermint flavor are dry blended. The blend is is filled into 4 oz bottle with a 100 ml calibration mark. At time of dispensing make up to volume with water and shake until all solids are dissolved. The mixture is refrigerated and used within 7 days.

The syrup can contain between 50 mg/5 ml and 500 mg/15 ml.

EXAMPLE 12

| Ingredient | Quantity |
| --- | --- |
| 1-(4-methoxybenzoyl)-5-oxo-2-pyrrolidinepropanoic acid | 150 g |
| Lactose | 1124 g |
| Corn Starch | 39 g |
| Hydroxypropyl cellulose | 30 g |
| Magnesium stearate | 7 g |
| Ethanol-water 50:50 | qs |

The 1-(4-methoxybenzoyl)-5-oxo-2-pyrrolidinepropanoic acid, lactose, and hydroxypropyl cellulose are blended and granulated with 50:50 ethanol-water. The wet granulation is screened, dried, and rescreened. The resulting dried granulation is blended with magnesium stearate and the corn starch and the mixture is compressed into 225 mg tablets using an 11/32 inch standard concave punch. Yield equals approximately 6000 tablets each containing 25.0 mg of 1-(4-methoxybenzoyl)-5-oxo-2-pyrrolidinepropanoic acid benzyl ester. Active ingredient can be varied to give tablets having 1, 2.5, 50 or 100 mg of active ingredient per tablet.

EXAMPLE 13

| Ingredient | Quantity |
| --- | --- |
| 1-(4-methoxybenzoyl)-5-oxo-2-pyrrolidinepropanoic acid | 15 g |
| Lactose | 1249 g |
| Corn Starch | 39 g |
| Hydroxypropyl cellulose | 30 g |
| Magnesium stearate | 7 g |
| Ethanol-water 50:50 | qs |

The 1-(4-methoxybenzoyl)-5-oxo-2-pyrrolidinepropanoic acid, lactose, and hydroxypropyl cellulose are blended and granulated with 50:50 ethanol-water. The wet granulation is screened, dried, and rescreened. The resulting dried granulation is blended with magnesium stearate and the corn starch and the mixture is compressed into 225 mg tablets using an 11/32 inch standard concave punch. Yield equals approximately 6000 tablets each containing 2.5 mg of 1-(4-methoxybenzoyl)-5-oxo-2-pyrrolidinepropanoic acid.

EXAMPLE 14

| Ingredient | Quantity |
| --- | --- |
| 1-(4-methoxybenzoyl)-5-oxo-2-pyrrolidinepropanoic acid | 6 g |
| Lactose | 1268 g |
| Corn Starch | 39 g |
| Hydroxypropyl cellulose | 30 g |
| Magnesium stearate | 7 g |
| Ethanol-water 50:50 | qs |

The 1-(4-methoxybenzoyl)-5-oxo-2-pyrrolidinepropanoic acid, lactose, and hydroxypropyl cellulose are blended and granulated with 50:50 ethanol-water. The wet granulation is screened, dried, and rescreened. The resulting dried granulation is blended with magnesium stearate and the corn starch and the mixture is compressed into 225 mg tablets using an 11/32 inch standard concave punch. Yield equals approximately 6000 tablets each containing 1.0 mg of 1-(4-methoxybenzoyl)-5-oxo-2-pyrrolidinepropanoic acid.

EXAMPLE 15

| Ingredient | Quantity |
| --- | --- |
| 1-(4-methoxybenzoyl)-5-oxo-2-pyrrolidinepropanoic acid | 300 g |
| Lactose | 974 g |
| Corn Starch | 39 g |
| Hydroxypropyl cellulose | 30 g |
| Magnesium stearate | 7 g |
| Ethanol-water 50:50 | qs |

1-(4-methoxybenzoyl)-5-oxo-2-pyrrolidinepropanoic acid, lactose, and hydroxypropyl cellulose are blended and granulated with 50:50 ethanol-water. The wet granulation is screened, dried, and rescreened. The resulting dried granulation is blended with magnesium stearate and the corn starch and the mixture is compressed into 225 mg tablets using an 11/32 inch standard concave punch. Yield equals approximately 6000 tablets each containing 50.0 mg of 1-(4-methoxybenzoyl)-5-oxo-2-pyrrolidinepropanoic acid.

EXAMPLE 16

| Ingredient | Quantity |
| --- | --- |
| 1-(4-methoxybenzoyl)-5-oxo-2-pyrrolidinepropanoic acid | 250 g |
| Lactose | 1723 g |

-continued

| Ingredient | Quantity |
|---|---|
| Magnesium stearate | 27 g |

The mixture is blended and filled into No. 4 hard gelatin capsules, filling each capsule with 200 mg of the powder mixture. Yield equals approximately 10,000 capsules each containing 25.0 mg of 1-(4-methoxybenzoyl)-5-oxo-2-pyrrolidinepropanoic acid.

EXAMPLE 17

| Ingredient | Quantity |
|---|---|
| 1-(4-methoxybenzoyl)-5-oxo-2-pyrrolidinepropanoic acid | 25 g |
| Lactose | 1948 g |
| Magnesium stearate | 27 g |

The mixture is blended and filled into No. 4 hard gelatin capsules, filling each capsule with 200 mg of the powder mixture. Yield equals approximately 10,000 capsules each containing 2.5 mg of 1-(4-methoxybenzoyl)-5-oxo-2-pyrrolidinepropanoic acid.

EXAMPLE 18

| Ingredient | Quantity |
|---|---|
| 1-(4-methoxybenzoyl)-5-oxo-2-pyrrolidinepropanoic acid | 10 g |
| Lactose | 1963 g |
| Magnesium stearate | 27 g |

The mixture is blended and filled into No. 4 hard gelatin capsules, filling each capsule with 200 mg of the powder mixture. Yield equals approximately 10,000 capsules each containing 1.0 mg 1-(4-methoxybenzoyl)-5-oxo-2-pyrrolidinepropanoic acid.

EXAMPLE 19

| Ingredient | Quantity |
|---|---|
| 1-(4-methoxybenzoyl)-5-oxo-2-pyrrolidinepropanoic acid | 500 g |
| Lactose | 1473 g |
| Magnesium stearate | 27 g |

The mixture is blended and filled into No. 4 hard gelatin capsules, filling each capsule with 200 mg of the powder mixture. Yield equals approximately 10,000 capsules each containing 50.0 mg of 1-(4-methoxybenzoyl)-5-oxo-2-pyrrolidinepropanoic acid.

EXAMPLE 20

| Ingredient | Quantity |
|---|---|
| 1-(4-methoxybenzoyl)-5-oxo-2-pyrrolidinepropanoic acid | 30 mg |
| Witepsol H35 | 1.97 g |

The Witepsol H35 is melted by heating to 38° C., 1-(4-methoxybenzoyl)-5-oxo-2-pyrrolidinepropanoic acid is added and mixed until thoroughly dispersed and placed in a mold at 33°-34° C. The composition of the suppository can be adjusted to contain from 30 to 500 mg of active ingredient.

EXAMPLE 21

| Ingredient | Quantity |
|---|---|
| 1-(4-methoxybenzoyl)-5-oxo-2-pyrrolidinepropanoic acid | 10 g |
| Saccarin Sodium | 0.5 g |
| Thihydroxysterain | 0.75 g |
| Propylparaben | 0.1 g |
| Imitation Cherry Flavor | 2 ml |
| Neobee M-5 qs ad | 100 ml |

Propylparaben is dissolved in a portion of the Neobee M-5, the trihydroxystearin is added and the mixture is homogenized for 30 minutes while maintaining the temperature between 50°-60° C. The mixture is cooled and the 1-(4-methoxybenzoyl)-5-oxo-2-pyrrolidinepropanoic acid, saccharin sodium, and imitation cherry flavor are added. The volume is made up with Neobee M-5.

EXAMPLE 22

| Ingredient | Quantity |
|---|---|
| 1-(4-methoxybenzoyl)-5-oxo-2-pyrrolidinepropanoic acid | 10 g |
| Sugar granulated, Bottlers grade | 60 g |
| Artificial Peppermint Flavor, Water Soluble (American Flavor and Fragrance) | 0.4 g |
| Water qs ad | 100 ml |

The 1-(4-methoxybenzoyl-5-oxo-2-pyrrolidinepropanoic acid, granulated sugar, and artificial peppermint flavor are dry blended. The blend is filled into a four ounce bottle with a 100 ml calibration mark. At time of dispensing make up to volume with water and shake until all solids are dissolved. The mixture is refrigerated and used within seven days.

EXAMPLE 23

| Ingredient | Quantity |
|---|---|
| 1-(4-methoxybenzoyl)-5-oxo-2-pyrrolidinepropanoic acid benzyl ester | 150 g |
| Lactose | 1124 g |
| Corn Starch | 39 g |
| Hydroxypropyl cellulose | 30 g |
| Magnesium stearate | 7 g |
| Ethanol-water 50:50 | qs |

The 1-(4-methoxybenzoyl)-5-oxo-2-pyrrolidinepropanoic acid benzyl ester, lactose, and hydroxypropyl cellulose are blended and granulated with 50:50 ethanol-water. The wet granulation is screened, dried, and rescreened. The resulting dried granulation is blended with magnesium stearate and the corn starch and the mixture is compressed into 225 mg tablets using an 11/32 inch standard concave punch. Yield equals approximately 6000 tablets each containing 25.0 mg of 1-(4-methoxybenzoyl)-5-oxo-2-pyrrolidinepropanoic acid benzyl ester.

EXAMPLE 24

| Ingredient | Quantity |
|---|---|
| 1-(4-methoxybenzoyl)-5-oxo-2-pyrrolidinepropanoic acid | 15 g |

-continued

| Ingredient | Quantity |
|---|---|
| benzyl ester | |
| Lactose | 1249 g |
| Corn Starch | 39 g |
| Hydroxypropyl cellulose | 30 g |
| Magnesium stearate | 7 g |
| Ethanol-water 50:50 | qs |

The 1-(4-methoxybenzoyl)-5-oxo-2-pyrrolidinepropanoic acid benzyl ester, lactose, and hydroxypropyl cellulose are blended and granulated with 50:50 ethanol-water. The wet granulation is screened, dried, and rescreened. The resulting dried granulation is blended with magnesium stearate and the corn starch and the mixture is compressed into 225 mg tablets using an 11/32 inch standard concave punch. Yield equals approximately 6000 tablets each containing 2.5 mg of 1-(4-methoxybenzoyl)-5-oxo-2-pyrrolidinepropanoic acid benzyl ester.

EXAMPLE 25

| Ingredient | Quantity |
|---|---|
| 1-(4-methoxybenzoyl)-5-oxo-2-pyrrolidinepropanoic acid benzyl ester | 6 g |
| Lactose | 1268 g |
| Corn Starch | 39 g |
| Hydroxypropyl cellulose | 30 g |
| Magnesium stearate | 7 g |
| Ethanol-water 50:50 | qs |

The 1-(4-methoxybenzoyl)-5-oxo-2-pyrrolidinepropanoic acid benzyl ester, lactose, and hydroxypropyl cellulose are blended and granulated with 50:50 ethanol-water. The wet granulation is screened, dried, and rescreened. The resulting dried granulation is blended with magnesium stearate and the corn starch and the mixture is compressed into 225 mg tablets using an 11/32 inch standard concave punch. Yield equals approximately 6000 tablets each containing 1.0 mg of 1-(4-methoxybenzoyl)-5-oxo-2-pyrrolidinepropanoic acid benzyl ester.

EXAMPLE 26

| Ingredient | Quantity |
|---|---|
| 1-(4-methoxybenzoyl)-5-oxo-2-pyrrolidinepropanoic acid benzyl ester | 300 g |
| Lactose | 974 g |
| Corn Starch | 39 g |
| Hydroxypropyl cellulose | 30 g |
| Magnesium stearate | 7 g |
| Ethanol-water 50:50 | qs |

The 1-(4-methoxybenzoyl)-5-oxo-2-pyrrolidinepropanoic acid benzyl ester, lactose, and hydroxypropyl cellulose are blended and granulated with 50:50 ethanol-water. The wet granulation is screened, dried, and rescreened. The resulting dried granulation is blended with magnesium stearate and the corn starch and the mixture is compressed into 225 mg tablets using an 11/32 inch standard concave punch. Yield equals approximately 6000 tablets each containing 50.0 mg of 1-(4-methoxybenzoyl)-5-oxo-2-pyrrolidinepropanoic acid benzyl ester.

EXAMPLE 27

| Ingredient | Quantity |
|---|---|
| 1-(4-methoxybenzoyl)-5-oxo-2-pyrrolidinepropanoic acid benzyl ester | 250 g |
| Lactose | 1723 g |
| Magnesium stearate | 27 g |

The mixture is blended and filled into No. 4 hard gelatin capsules, filling each capsule with 200 mg of the powder mixture. Yield equals approximately 10,000 capsules each containing 25.0 mg of 1-(4-methoxybenzoyl)-5-oxo-2-pyrrolidinepropanoic acid benzyl ester.

EXAMPLE 28

| Ingredient | Quantity |
|---|---|
| 1-(4-methoxybenzoyl)-5-oxo-2-pyrrolidinepropanoic acid benzyl ester | 25 g |
| Lactose | 1948 g |
| Magnesium stearate | 27 g |

The mixture is blended and filled into No. 4 hard gelatin capsules, filling each capsule with 200 mg of the powder mixture. Yield equals approximately 10,000 capsules each containing 2.5 mg of 1-(4-methoxybenzoyl)-5-oxo-2-pyrrolidinepropanoic acid benzyl ester.

EXAMPLE 29

| Ingredient | Quantity |
|---|---|
| 1-(4-methoxybenzoyl)-5-oxo-2-pyrrolidinepropanoic acid benzyl ester | 500 g |
| Lactose | 1473 g |
| Magnesium stearate | 27 g |

The mixture is blended and filled into No. 4 hard gelatin capsules, filling each capsule with 200 mg of the powder mixture. Yield equals approximately 10,000 capsules each containing 50.0 mg of 1-(4-methoxybenzoyl)-5-oxo-2-pyrrolidinepropanoic acid benzyl ester.

EXAMPLE 30

| Ingredient | Quantity |
|---|---|
| 1-(4-methoxybenzoyl)-5-oxo-2-pyrrolidinepropanoic acid benzyl ester | 30 mg |
| Witepsol H35 | 1.97 g |

The Witepsol H35 is melted by heating to 38° C., 1-(4-methoxybenzoyl)-5-oxo-2-pyrrolidinepropanoic acid benzyl ester is added and mixed until thoroughly dispersed and placed in a mold at 33°–34° C.

EXAMPLE 31

| Ingredient | Quantity |
|---|---|
| 1-(4-methoxybenzoyl)-5-oxo-2-pyrrolidinepropanoic acid benzyl ester | 10 g |
| Saccharin Sodium | 0.5 g |
| Trihydroxystearin | 0.75 g |
| Propylparaben | 0.1 g |

-continued

| Ingredient | Quantity |
|---|---|
| Imitation Cherry Flavor | 2 ml |
| Neobee M-5 q.s. ad | 100 ml |

Propylparaben is dissolved in a portion of the Neobee M-5, the trihydroxystearin is added and the mixture is homogenized for 30 minutes while maintaining the temperature between 50°-60° C. The mixture is cooled and the 1-(4-methoxybenzoyl)-5-oxo-2-pyrrolidinepropanoic acid benzyl ester, saccharin sodium, and imitation cherry flavor are added. The volume is made up with Neobee M-5.

EXAMPLE 31

| Ingredient | Quantity |
|---|---|
| 1-(4-methoxybenzoyl)-5-oxo-2-pyrrolidinepropanoic acid benzyl ester | 10 g |
| Sugar granulated, Bottlers grade | 60 g |
| Artificial Peppermint Flavor, Water Soluble (American Flavor and Fragrance) | 0.4 g |
| Water q.s. ad | 100 ml |

The 1-(4-methoxybenzoyl)-5-oxo-2-pyrrolidinepropanoic acid benzyl ester, granulated sugar, and artificial peppermint flavor are dry blended. The blend is is filled into 4 oz bottle with a 100 ml calibration mark. At time of dispensing make up to volume with water and shake until all solids are dissolved. The mixture is refrigerated and used within 7 days.

I claim:

1. A compound of the formula

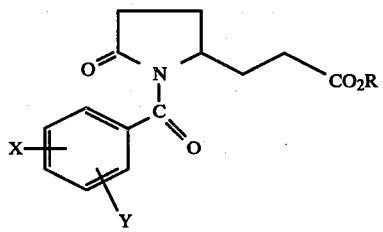

wherein R is hydrogen and the pharmaceutically acceptable metal or amine salts thereof, alkyl or

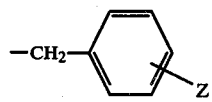

where Z is hydrogen alkyl, fluoro, chloro, bromo, or trifluoromethyl; X and Y are hydrogen, chloro, fluoro, hydroxy, amino, alkylamino, dialkylamino, methyl, alkoxy having from one to six carbon atoms or benzyloxy; wherein X and Y may be the same or different with the proviso that when R is hydrogen, or a pharmaceutically acceptable metal or amine cation, X is a substituent other then hydrogen.

2. The compounds of claim 1 wherein R is hydrogen, methyl, ethyl, benzyl, 2-chlorobenzyl, 3-chlorobenzyl, 4-chlorobenzyl, 4-trifluoromethylbenzyl, 4-methylbenzyl, sodium, potassium, calcium, ammonium, trimethylammonium or triethylammonium; X is 2-fluoro, 4-chloro, 4-fluoro, 2-methoxy, 3-methoxy, 3-methyl, Y-methoxy and Y is hydrogen; X is 3-benzyloxy or 3-hydroxy, 3-methyl and Y is 4-methoxy.

3. The compounds of claim 1 wherein R is hydrogen, sodium, potassium, calcium, magnesium or ammonium; X is 4-fluoro, 4-methoxy or 4-chloro and Y is hydrogen.

4. The compound of claim 1 having the name 1-(4-Methoxybenzoyl)-5-oxo-2-pyrrolidinepropanoic acid and pharmaceutically acceptable metal or amine salts.

5. The compound of claim 1 having the name 1-(3-Methoxybenzoyl)-5-oxo-2-pyrrolidinepropanoic acid and pharmaceutically acceptable metal or amine salts.

6. The compound of claim 1 having the name 1-(2-Methoxybenzoyl)-5-oxo-2-pyrrolidinepropanoic acid and pharmaceutically acceptable metal or amine salts.

7. The compound of claim 1 having the name 1-(3-Hydroxy-4-methoxybenzoyl)-5-oxo-2-pyrrolidinepropanoic acid and pharmaceutically acceptable metal or amine salts.

8. The compound of claim 1 having the name 1-(4-Fluorobenzoyl)-5-oxo-2-pyrrolidinepropanoic acid and pharmaceutically acceptable metal or amine salts.

9. The compound of claim 1 having the name 1-(2-Fluorobenzoyl)-5-oxo-2-pyrrolidinepropanoic acid and pharmaceutically acceptable metal or amine salts.

10. The compound of claim 1 having the name 1-(4-Chlorobenzoyl)-5-oxo-2-pyrrolidinepropanoic acid and pharmaceutically acceptable metal or amine salts.

11. The compound of claim 1 having the name 1-(2-Chlorobenzoyl)-5-oxo-2-pyrrolidinepropanoic acid and pharmaceutically acceptable metal or amine salts.

12. The compound of claim 1 having the name 1-(4-Methoxybenzoyl)-5-oxo-2-pyrrolidinepropanoic acid benzyl ester.

13. The compound of claim 1 having the name 1-(3-Methoxybenzoyl)-5-oxo-2-pyrrolidinepropanoic acid benzyl ester.

14. The compound of claim 1 having the name 1-(2-Methoxybenzoyl)-5-oxo-2-pyrrolidinepropanoic acid benzyl ester.

15. The compound of claim 1 having the name 1-(3-Hydroxy-4-methoxybenzoyl)-5-oxo-2-pyrrolidinepropanoic acid benzyl ester.

16. The compound of claim 1 having the name 1-(4-Fluorobenzoyl)-5-oxo-2-pyrrolidinepropanoic acid benzyl ester.

17. The compound of claim 1 having the name 1-(2-Fluorobenzoyl)-5-oxo-2-pyrrolidinepropanoic acid benzyl ester.

18. The compound of claim 1 having the name 1-(4-Chlorobenzoyl)-5-oxo-2-pyrrolidinepropanoic acid benzyl ester.

19. The compound of claim 1 having the name 1-(2-Chlorobenzoyl)-5-oxo-2-pyrrolidinepropanoic acid benzyl ester.

20. The compound of claim 1 having the name 1-(4-methoxy-3-methylbenzoyl)-5-oxo-2-pyrrolidinepropanoic acid and pharmaceutically acceptable metal or amine salts.

* * * * *